US00PP34143P2

(12) United States Plant Patent
Eveleens et al.

(10) Patent No.: US PP34,143 P2
(45) Date of Patent: Apr. 19, 2022

(54) ***HYDRANGEA* PLANT NAMED 'HOKOMABEBOS'**

(50) Latin Name: *Hydrangea macrophylla*
Varietal Denomination: Hokomabebos

(71) Applicants: Kolster Holding B.V., Boskoop (NL); Horteve Breeding B.V., Aalsmeer (NL)

(72) Inventors: Cornelis Pieter Eveleens, Aalsmeer (NL); Peter Rudolf Kolster, Boskoop (NL)

(73) Assignees: HORTEVE BREEDING BV, Aalsmeer (NL), part interest; KOLSTER HOLDING BV, Boskoop (NL), part interest ( * ) Notice: Subject to any disclaimer, the term of this patent is extended or adjusted under 35 U.S.C. 154(b) by 0 days.

(21) Appl. No.: 17/372,452

(22) Filed: Jul. 10, 2021

(30) Foreign Application Priority Data

May 26, 2021 (CA) ..... 21-10545

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48
See application file for complete search history.

*Primary Examiner* — Anne Marie Grunberg
(74) *Attorney, Agent, or Firm* — Penny J. Aguirre

(57) ABSTRACT

A new cultivar of *Hydrangea macrophylla* plant named 'Hokomabebos' that is characterized by its large mophead inflorescences, its inflorescences with sterile sepals that are picotee (bicolor) with white centers and pink-red edges, its dark colored leaves, and its suitability for growing in containers.

2 Drawing Sheets

Botanical classification: *Hydrangea macrophylla.*
Varietal denomination: 'Hokomabebos'.

CROSS-REFERENCE TO A RELATED APPLICATION

This application claims priority to a Canadian Plant Breeder's Rights Application No. 21-10545 filed on May 26, 2021, under 35 U.S.C. 119(f), the entire contents of which is incorporated by reference herein.

BACKGROUND OF THE INVENTION

The present invention relates to a new and distinct cultivar of *Hydrangea macrophylla* and will be referred to hereafter by its cultivar name, 'Hokomabebos'. 'Hokomabebos' represents a new mophead type *Hydrangea*, a deciduous shrub grown for use as a landscape plant.

'Hokomabebos' was derived from an ongoing breeding program conducted by the Inventors in Boskoop, The Netherlands. The objectives of the breeding program are to develop new cultivars of *Hydrangea macrophylla* with bicolor and light colored inflorescences (almost white flowers with a red edge), and dark foliage colors.

The Inventor made a controlled cross in March of 2011 in Boskoop, The Netherlands between unnamed and unpatented proprietary plants from their breeding program; female parent (ref. code 07-036-01) and male parent (ref. code 07-120-09). 'Hokomabebos' was selected in May of 2013 as a single unique plant amongst the resulting seedlings.

Asexual propagation of the new cultivar was first accomplished under the direction of the Inventors by stem cuttings in July of 2013 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomabebos' as a unique cultivar of *Hydrangea.*

1. 'Hokomabebos' exhibits large mophead inflorescences.
2. 'Hokomabebos' exhibits inflorescences with sterile sepals that are picotee (bicolor) with white centers and pink-red edges.
3. 'Hokomabebos' exhibits dark colored leaves.
4. 'Hokomabebos' exhibits suitability for growing in containers.

The female parent of 'Hokomabebos' differs from 'Hokomabebos' in having leaves that are greener in color and inflorescences with sterile sepals that are all pink in color and not picotee. The male parent of 'Hokomabebos' differs from 'Hokomabebos' in having leaves that are less dark in color and inflorescences with sterile sepals that are near white with a thin pink edge in color. 'Hokomabebos' can be most closely compared to the *Hydrangea macrophylla* cultivars 'Hortfire' (U.S. Plant Pat. No. 29,058) and 'Hortmaflam' (U.S. Plant Pat. No. 27,716). Both 'Hortfire' and 'Hortmaflam' are similar to 'Hokomabebos' in having dark color leaves and inflorescences with sterile sepals that are picotee. 'Hortfire' differs from 'Hokomabebos' in having inflorescences with sterile sepal that are less picotee and margins that are curly and dented, and leaves that are lighter in color. 'Hortmaflam' differs from 'Hokomabebos' in having leaves that are lighter in color and inflorescences with sterile sepals that are white in color with and thin dark pink and dented margins.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Wayside Gardens, Blooming Easy Plants, Jackson and Perkins, Prides Corner, Savvy Gardening, Van Zyverden, Target, HSN, QVC, Walmart, Home Depot, Suburban Lawn and Garden, Mackeys Grow, Plants Nouveau, Van Belle Nurseries, and Greenhouse Magazine.

BRIEF DESCRIPTION OF THE DRAWINGS

The accompanying color photographs illustrates the overall appearance and distinct characteristics of the new *Hydrangea*. The photographs were taken of a two-year-old plant as grown outdoors in a 1-gallon container in Abbotsford, British Columbia, Canada.

The photograph in FIG. 1 provides a side view of the plant habit of 'Hokomabebos' in bloom.

Figure 1:
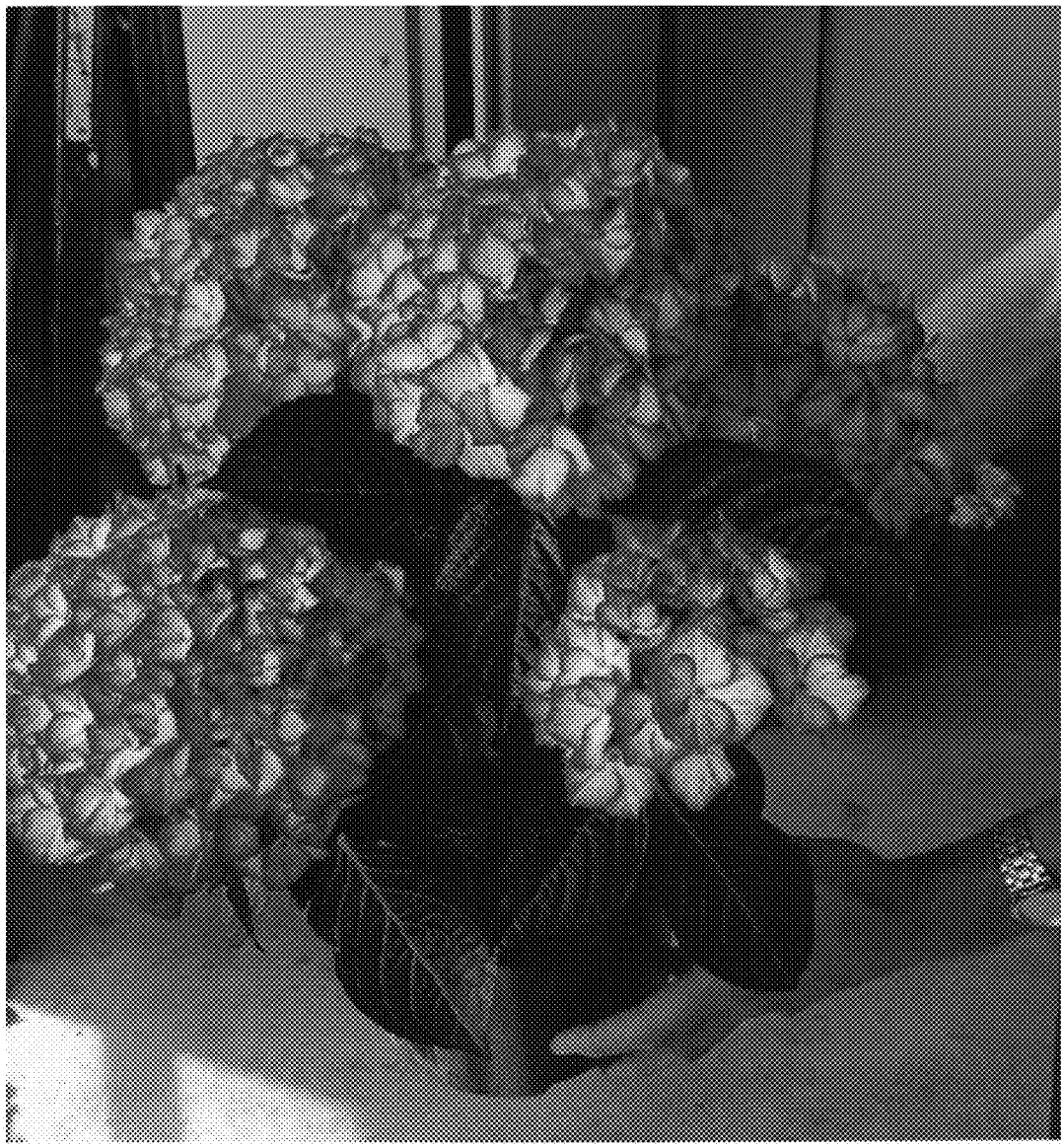
Figure 2:
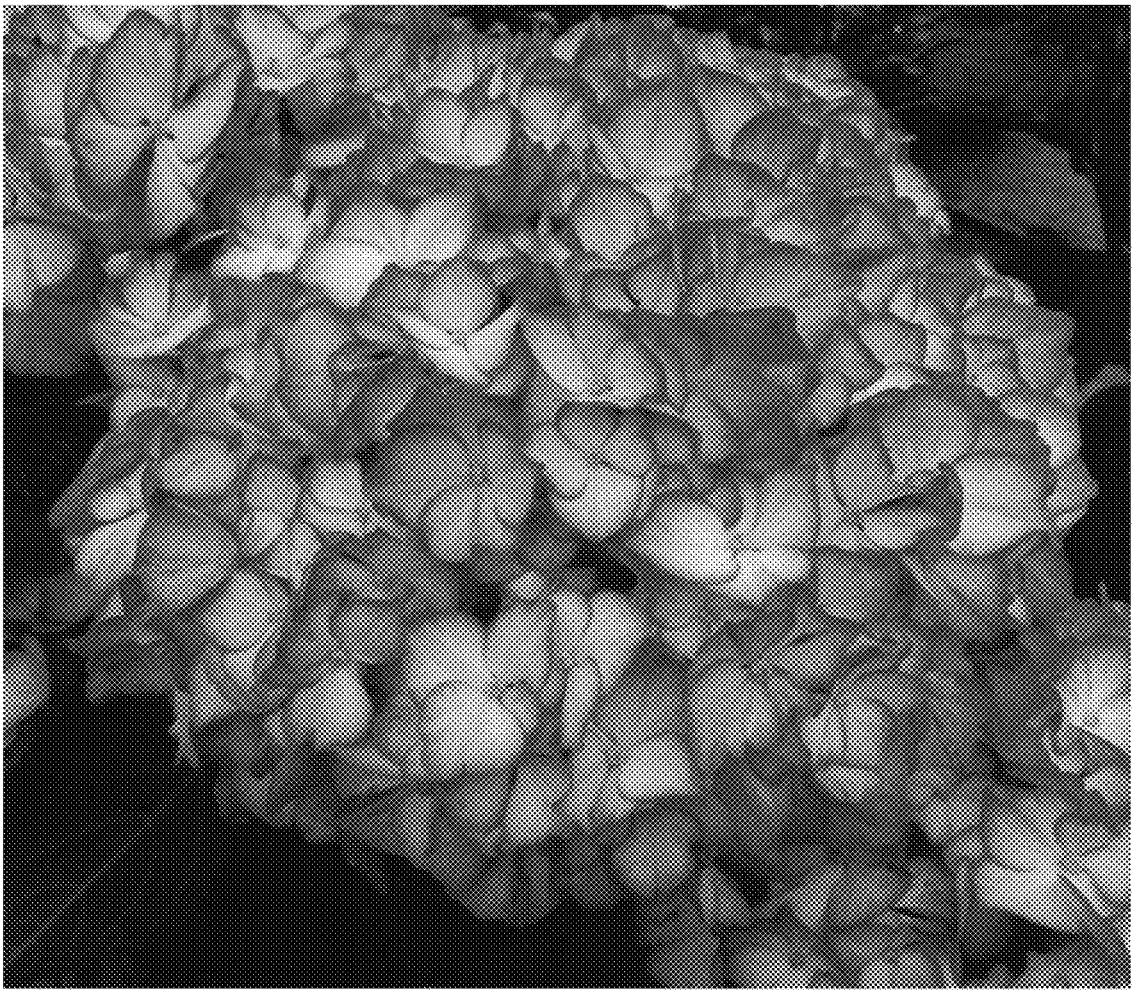

The photograph in FIG. 2 provides a close-up view of an inflorescence of 'Hokomabebos'.

The colors in the photographs may differ slightly from the color values cited in the detailed botanical description, which accurately describe the colors of the new *Hydrangea*.

BOTANICAL DESCRIPTION OF THE PLANT

The following is a detailed description of 15-month-old plants of 'Hokomabebos' as grown outdoors in 1-gallon containers in Abbotsford, British Columbia, Canada. The plants were grown under non-blueing conditions and blueing conditions have not been used. The color determination is in accordance with The 2015 Colour Chart of The Royal Horticultural Society, London, England, except where general color terms of ordinary dictionary significance are used.

General description:

*Blooming period*.—At least 2 months in mid-summer in The Netherlands.

*Plant type*.—Deciduous shrub, mophead type *Hydrangea*.

*Plant habit*.—Compact, suitable for container growing.

*Height and spread*.—Reaches about 27 cm in height and 45 cm in spread as grown in a 1-gallon container, reaches 100 cm in height and width as grown as a 3-year-old plant in the landscape.

*Hardiness*.—At least to U.S.D.A. Zones 5 to 9.

*Diseases and pests*.—No resistance or susceptibility to diseases or pests has been observed.

*Root description*.—Fine and fibrous, NN155B in color.

*Propagation*.—Softwood stem cuttings.

*Growth rate*.—Moderate.

*Root development*.—Time required for root initiation is 6 weeks, time required to produce a young plant from rooted cutting is 18 weeks.

Stem description:

*Stem shape*.—Rounded.

*Stem strength*.—Strong.

*Stem color*.—Young and mature; 144A in color, mature bark; color is a blend of 199A and N200A.

*Stem size*.—Main branches; average of 9 cm in length, 5 mm in diameter, lateral branches; average of 5.5 cm in length, 4 mm in diameter.

*Stem surface*.—Younger and mature stems; glabrous and slightly glossy, lenticellate, lenticles; very sparse 5 per $cm^2$, an average of 1 mm in length and 0.3 mm in width, 200C in color, old growth at base; bark-like, mostly smooth and can be slightly exfoliating.

*Internode length*.—Average of 4 cm.

*Branching*.—Average of 4 main branches, average of 4 to 6 lateral branches per main branch.

*Stipules*.—Persistent, 2 opposite at base of petioles, stipule bud; is 2 mm in length, 1 mm in width, 187A in color, oblong in shape, acute apex, glossy and glabrous surface.

Foliage description:

*Leaf shape*.—Elliptical.

*Leaf arrangement*.—Opposite.

*Leaf division*.—Simple.

*Leaf base*.—Attenuate.

*Leaf apex*.—Apiculate.

*Leaf margins*.—Serrate.

*Leaf venation*.—Pinnate, upper and lower surface; 145A and 145B.

*Leaf size*.—Average of 10.5 cm in length and 6 cm in width.

*Leaf attachment*.—Petiolate.

*Leaf surface*.—Upper and lower surface slightly glossy.

*Leaf color*.—Young upper and lower surface; 200A, slightly flushed with 144A, mature upper surface 144A, flushed with 200A, margins 200A, mature lower surface 147B.

*Petioles*.—An average of 1 cm in length and 3 mm in diameter, both surfaces slightly glossy and 144A in color.

Inflorescence description:

*Inflorescence type*.—Terminal panicle, full rounded mophead in form, comprised of single sterile flowers and inconspicuous fertile flowers.

*Lastingness of inflorescence*.—Persistent at least 2 months in color.

*Inflorescence number*.—One per lateral.

*Inflorescence size*.—Average of 15 cm in height, 23 cm in diameter.

*Flower number*.—Average of 85 sterile flowers and 15 fertile flowers per panicle.

*Flower fragrance*.—Very faint, floral rose fragrance.

*Flower aspect*.—Upright to outward.

*Flower size*.—Sterile flowers; an average of 5 cm in diameter, 3 cm in depth, fertile flowers; an average of 1 cm in diameter and 5 mm in depth.

*Flower type*.—Rotate.

*Flower buds*.—Sterile flowers; average of 3 mm in length and diameter, rounded, flattened in shape, color; base NN155C, center 68A, top and margins 79A, fertile flowers; average of 3 mm in length and diameter, rounded in shape, color; base NN155C and flushed with 145A, center 68A, top and margins 79A.

*Peduncles*.—Moderately strong, average of 3 cm in length and 3 mm in width, color; 144A, with random blotches of 187A, surface is slightly glossy to matte, smooth.

*Pedicels*.—Moderately strong, average of 2 cm in length and 2 mm in width, color; young pedicels 142B, occasionally speckled with 185A in color, mature pedicels 159A in color, occasionally speckled with 187C in color, surface is matte and moderately covered with very fine woolly hairs that match surface color.

*Petals*.—Sterile flowers; 5, rotate, 3 mm in length, 2 mm in diameter, linear in shape, acute apex, cuneate base, entire margins, cup-shaped, glabrous and matte surface, young and mature color upper and lower surface N155C, tip flushed with 71A, fertile flowers; 5, rotate, 5 mm in length, 3 mm in diameter, linear in shape, acute apex, cuneate base, entire margins, cup-shaped, glabrous and matte surface, young and mature color upper and lower surface N155C, tip and margins flushed with 71B.

*Sepals*.—Sterile flowers; showy, 4, deltoid to reniform in shape, moderately to strongly overlapping, rotate in arrangement, entire margins moderately undulate, apex is very slightly retuse to bluntly pointed with 2 points, cuneate base, average of 3.5 cm in length and 5 cm in width, upper and lower surface glabrous and satiny, color: when opening upper and lower surface; base 1C, veins 1C and 157A, centers 185A, margins 187A, when fully open upper surface; base, 62A and NN155C, veins NN155C, outside edges 63A, margins 61A, when fully open lower surface; base, 62A, veins N155B and flushed with 76C, outside edges 58D, margins very slightly flushed with N79B, both surfaces fading to a blend of N79A and N79C at the outside edges and margins, base 69A, center 163B to 163C, fertile flowers; 5 to 6, rotate in arrangement, ovate to broadly ovate in shape, entire to very slightly serrate margins, acute apex, cuneate base, average of 6 mm in length and 3 mm in width, both surfaces are glabrous, color; young upper and lower surface 145A, mature upper and lower surface 158B, flushed with 157A, 145A and 75D.

Reproductive organs:

*Stamens*.—Sterile flowers; average of 7, anther is broad reniform in shape, 0.5 mm in diameter and 8D in color, filament is 3 mm in length and NN155C in color, pollen is low in quantity, fertile flowers; average of 7, anther is broad reniform in shape, 0.7 mm in length and 8D, filament is 4 mm in length and NN155C in color, pollen is low in quantity and too small amount for color reading.

*Pistils*.—Sterile flowers; average of 3, an average of 2 mm in length, stigma is club-shaped, 1 mm in diameter and NN155C in color, style is NN155C in color, ovary is 8D in color and inferior, fertile flowers; average of 3, an average of 2 mm in length, stigma is clavate in shape and NN155C in color, style is NN155C in color, ovary is 16D in color and inferior.

*Fruit and seed*.—Not observed to date.

It is claimed:

1. A new and distinct cultivar of *Hydrangea* plant named 'Hokomabebos' substantially as herein illustrated and described.

* * * * *